United States Patent [19]
Dolle et al.

[11] Patent Number: 5,565,430
[45] Date of Patent: Oct. 15, 1996

[54] AZAASPARTIC ACID ANALOGS AS INTERLEUKIN-1β CONVERTING ENZYME INHIBITORS

[75] Inventors: Roland E. Dolle, King of Prussia; Todd L. Graybill, Pottstown, both of Pa.

[73] Assignee: Sterling Winthrop Inc., New York, N.Y.

[21] Appl. No.: 284,861

[22] Filed: Aug. 2, 1994

[51] Int. Cl.[6] .................. A61K 31/195; A61K 38/05; C07C 229/02; C07K 5/062
[52] U.S. Cl. .................. 514/19; 514/119; 514/407; 514/471; 514/542; 514/551; 514/563; 514/565; 548/370.1; 549/318; 560/37; 560/169; 562/442; 562/561
[58] Field of Search .................. 530/323, 331; 514/18, 19, 20, 119, 407, 471, 542, 551, 563, 565; 548/370.1; 549/318; 560/37, 169; 562/442, 561

[56] References Cited

U.S. PATENT DOCUMENTS 5,430,128  7/1995  Chapman et al. .................. 530/330
5,434,248  7/1995  Chapman et al. .................. 530/330

OTHER PUBLICATIONS

Bioorg. Med. Chem. Lett., vol. 2, No. 6, issued 1992, Chapman, "Synthesis of a Potent, Reversible Inhibitor . . . ", pp. 613–618.
Chem. Ber., vol. 102, issued 1969, Niedrich, "Synthese von substituierten 2.4–Bis . . . ", pp. 1557–1569.
Tet. Letters, vol. 26, No. 26, issued 1985, Moody et al, "Synthesis of Aza–β–Lactams by Rhodium . . . ", pp. 3171–3172.
Chemical Abstracts 78: 72578c (1973).
Chemical Abstracts 88:38140a (1978).

*Primary Examiner*—Jeffrey E. Russel
*Attorney, Agent, or Firm*—William J. Davis; Paul E. Dupont

[57] ABSTRACT

Disclosed are compounds, compositions and methods for inhibiting interleukinprotease activity. The compounds, α-substituted acetamides a

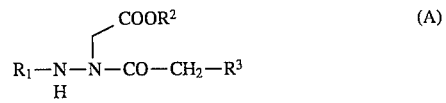

(A)

wherein:
$R_2$=H or alkyl;
$R^3$=halo, $O(CO)_{0-1}$ aryl, $OPOR^4R^5$;

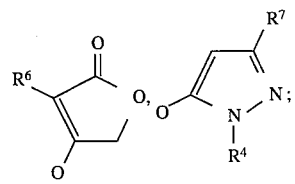

where
$R^4$ and $R^5$=aryl;
$R^6$=H, aryl or aralkyl;
$R^7$=independently selected from $R^6$, $CF_3$ and $CF_2CF_3$;
$R^1$=$R^6$-CO, heteroaryl-CO, heteroaralkyl-CO and amino acid.

9 Claims, No Drawings

AZAASPARTIC ACID ANALOGS AS INTERLEUKIN-1β CONVERTING ENZYME INHIBITORS

BACKGROUND OF THE INVENTION

1. Field of the Invention

This invention relates to a series of azaaspartic acid analogs which exhibit in vitro and in vivo inhibition of interleukin-1β convening enzyme, to compositions containing the novel aspartic acid analogs and to methods for therapeutic utility. More particularly, the interleukin 1β converting enzyme inhibitors described in this invention comprise novel azaaspartic acid α-substituted acetamides which possess particular utility in the treatment of inflammatory and immune-based diseases of lung, central nervous system, and connective tissues.

2. Reported Developments

Interleukin 1β (IL-1β) protease (also known as interleukin-1β converting enzyme or ICE) is the enzyme responsible for processing of the biologically inactive 31 kD precursor IL-1β to the biologically active 17 kD form (Kostura, M. J.; Tocci, M. J.; Limjuco, G.; Chin, J.; Cameron, P.; Hillman, A. G.; Chartrain, N. A.; Schmidt, J. A., *Proc. Nat. Acad. Sci.* (1989), 86, 5227–5231 and Black, R. A.; Kronheim, S. R.; Sleath, P. R., *FEBS Let.*, (1989), 247, 386–391). In addition to acting as one of the body's early responses to injury and infection, IL-1β has also been proposed to act as a mediator of a wide variety of diseases, including rheumatoid arthritis, osteoarthritis, inflammatory bowel disease, sepsis, acute and chronic myelogenous leukemia and osteoporosis (Dinarello, C. A.; Wolff, S. M., *New Engl. J. Med.*, (1993), 328, 106). A naturally occurring IL-1β receptor antagonist has been used to demonstrate the intermediacy of IL-1β in a number of human diseases and animal models (Hannum, C. H.; Wilcox, C. J.; Arend, W. P.; Joslin, G. G.; Ddpps, D. J.; Heimdal, P. L.; Armes, L. G.; Sommer, A.; Eisenberg, S. P.; Thompson, R. C., *Nature*, (1990), 343, 336–340; Eisenberg, S. P.; Evans, R. J.; Arend, W. P.; Verderber, E.; Brewer, M. T.; Hannum, C. H.; Thompson, R. C., *Nature* (1990), 343, 341–346; Ohlsson, K.; Bjork, P.; Bergenfeldt, M.; Hageman, R.; Thompson, R. C., *Nature*, (1990), 348, 550–552; Wakabayashi, G., *FASEB*, (1991), 338–343; Pacifici, R.; et al. *Proc. Natl. Acad. Sci.* (1989), 86, 2398–2402 and Yamamoto, I.; et al. *Cancer Rsh* (1989), 49, 4242–4246). The specific role of IL-1β in inflammation and immunomodulation is supported by the recent observation that the cowpox virus employs an inhibitor of ICE to suppress the inflammatory response of its host (Ray, C. A. et al, *Cell*, (1992), 69,597–604).

The importance of these observations is well recognized by those skilled in the art and several workers have proposed and demonstrated in vivo the utility of ICE inhibitors in modifying certain IL-1β mediated disease states. Some have suggested the development and therapeutic use of a small molecule inhibitor of mature IL-1β formation (See, e.g., Miller, D. K. et al. "The IL-1β Converting Enzyme as a Therapeutic Target" in Immunosuppressive and Antiinflammatory Drugs; *Annals of the New York Academy of Sciences;* Vol. 696, pp133–148, 1993). The following review of the current state of the art in ICE research further supports such utility of ICE inhibitors:

1) WO 9309135, published 11 May 1993, teaches that peptide-based aspartic acid arylacyloxy-and aryoxymethyl ketones are potent inhibitors of ICE in vitro. These compounds also specifically inhibited ICE in the whole cell (in vivo) by their ability to inhibit the formation of mature IL-1β in whole cells. These ICE inhibitors also demonstrated utility in reducing fever and inflammation/swelling in rats.

2) Patients with Lyme disease sometimes develop Lyme arthritis. *B. Burgdorferi*, the causative agent of Lyme disease, is a potent inducer of IL-1 synthesis by mononuclear cells. Miller et al. (Miller, L. C.; Lynch, E. A. Isa, S.; Logan, J. W.; Dinarello, C. A.; and Steere, A. C., "Balance of synovial fluid IL-1β and IL-1 Receptor Antagonist and Recovery from Lyme arthritis", *Lancet* (1993) 341; 146–148) showed that in patients who recovered quickly from Lyme Arthritis, the balance in synovial fluid of IL-1β and IL-1ra was in favor of IL-ra. When the balance was shifted in favor of IL-1β, it took significantly longer for the disease to resolve. The conclusion was that the excess IL-1ra blocked the effects of the IL-1 β in the patients studied.

3) IL-1 is present in affected tissues in ulcerative colitis in humans. In animal models of the disease, IL-1β levels correlate with disease severity. In the model, administration of 1 L-1ra reduced tissue necrosis and the number of inflammatory cells in the colon. See, Cominelli, F.; Nast, C. C.; Clark, B. D.; Schindler, R., Llerena, R.; Eysselein, V. E.; Thompson, R. C.; and Dinarello, C. A.; "Interleukin-1 Gene Expression, Synthesis, and Effect of Specific IL-1 Receptor Blockade in Rabbit Immune Complex Colitis" *J. Clin. Investigations* (1990) Vol. 86, pp, 972–980.

4) The IL-1 receptor antagonist, Antril (Synergen), possess significant antiinflammatory activity in patients with active rheumatoid arthritis. In a multicenter Phase II dose ranging study, 175 patients received subcutaneous doses of Antril at 20mg, 70mg and 200mg seven times, three times or once per week. The antagonist was found to be most effective when taken daily. After three weeks of daily treatment, patients showed a decrease in joint swelling and less disease activity (Scrip, NO 1873, 1993).

5) IL-1ra supresses joint swelling in the PG-APS model of arthritis in rats. See Schwab, J. H.; Anderie, S. K.; Brown, R. R.; Dalldorf, F. G. and Thompson, R. C., "Pro- and Anti-Inflammatory Roles of Interleukin-1 in Recurrence of Bacterial Cell Wall-Induced Arthritis in Rats". *Infect. Immun.* (1991) 59; 4436–4442.

6) IL-1ra shows efficacy in a small open-label human Rheumatoid Arthritis trial. See, Lebsack, M. E.; Paul, C. C.; Bloedow, C. C.; Burch, F. X.; Sack, M. A.; Chase, W., and Catalano, M. A. "Subcutaneous IL-1 Receptor Antagonist in Patients with Rheumatoid Arthritis", Arth. Rheum. ( 1991 ) 34; 545.

7) Soluble IL-1 receptor significantly reduces clinically the cutaneous late-phase allergic reaction. This was demonstrated in a prospective, randomized, double-blind, placebo-controlled study on 15 allergic subjects. See, Mullarkey, M. F. et al. "Human Cutaneous Allergic Late-Phase Response is Inhibited by Soluble IL-1 Receptor", J. of Immunology, (1994) 152; 2033–2041.

8) IL-1 appears to be an autocrine growth factor for the proliferation of chronic myelogenous leukemia cells. Both IL-1ra and sIL-1R inhibit colony growth in cells removed from leukemia patients. See, Estrov, Z.; Kurzrock, R.; Wetzler, M.; Kantarjian, H.; Blake, M.; Harris, D.; Gutterman, J. U.; and Talpaz, M., "Suppression of Chronic Myelogenous Leukemia Colony Growth by Interleukin-1 (IL-1) Receptor Antagonist and Soluble IL-1 Receptors: a Novel Application for Inhibitors of IL-1 Activity". *Blood* (1991) 78; 1476–1484.

9) As in 6) above, but for acute myelogenous leukemia rather than chronic myelogenous leukemia. See, Estrov, Z.; Kurzrock, R.; Estey, E.; Wetzler, M.; Ferrajoli, A.; Harris, D.; Blake, M.; Guttermann, J. U.; and Talpaz, M. "Inhibition of Acute Myelogenous Leukemia Blast Proliferation by Interleukin-1 (IL-1) Receptor Antagonist and Soluble IL-1 Receptors". (1992) *Blood* 79; 1938–1945.

An effective therapy has yet to be fully developed commercially for the treatment of IL-1β mediated inflammatory diseases. Consequently, there is a need for therapeutic agents effective in the treatment and prevention of these diseases.

SUMMARY OF THE INVENTION

It is known that aspartic acid is the P1 specificity determinant for ICE. This is exemplified by the potent irreversible inhibitor i (structure 1) which contains a P1 aspartic acid residue. In this invention we describe inhibitors where the traditional aspartic acid residue is substituted with an azaaspartic acid residue as indicated by ii (structure 1). In these novel agents, the α-carbon atom which bears the aspartic acid side chain has been replaced by a nitrogen atom.

STRUCTURE 1

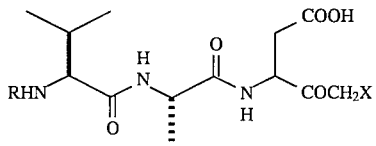
(i)

Aspartic Acid-Based ICE Inhibitor (Dolle, R. E. et al., J. Med. Chem. 37, 563 (1994))

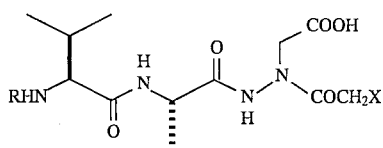
(ii)

Azaaspartic Acid-Based ICE Inhibitor (Present Invention)

According to the present invention, there is provided a compound of the formula (A) or a pharmaceutically acceptable salt thereof:

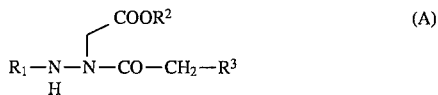
(A)

wherein:
$R_2$=H or alkyl;
$R_3$=halo, $O(CO)_{0-1}$ aryl, $OPOR^4R^5$;

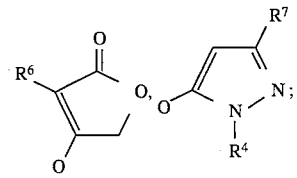

where
$R^4$ and $R^5$=aryl;
$R^6$=H, aryl or aralkyl;
$R^7$=independently selected from $R^6$, $CF_3$ and $CF_2CF_3$;

$R^1$=$R^6$-CO, heteroaryl-CO, heteroaralkyl-CO and amino acid.

"Alkyl" is defined as a saturated aliphatic hydrocarbon which may be either straight- or branched-chain. Preferred groups have no more than about 12 carbon atoms and may be methyl, ethyl and structural isomers of propyl, butyl, pentyl, hexyl, octyl, nonyl, decyl, undecyl, dodecyl.

"Aryl" is defined as a phenyl or naphthyl ring which may be substituted or unsubstituted wherein one or more of the hydrogen atoms has been replaced by the same or different substituents including halo, alkyl, aryl, nitro, cyano, amino, hydroxyl, alkoxy or haloalkyl.

"Aralkyl" means an alkyl radical substituted with an aryl ring, For example, benzyl. 4-chlorobenzyl.

"Heteroaryl" means pyridyl, thienyl or furanyl and structural isomers thereof.

"Heteroaralkyl" means an alkyl radical substituted by a heteroaryl ring. For example, 2-thienyl ethyl.

"Halo" means iodo, bromo, chloro, and fluoro.

"Amino acid" is defined as a commercially available natural or unnatural amino acid or dipeptide where the α-amino group in the amino acid or dipeptide has been protected with an N-protecting group. Such groups include, amides, sulfonamides, carbamates, and ureas as described in *The Peptides*, E. Gross and J. Meienhofer, Eds., Vol. 2, (1981) Academic Press, NY. N-Benzyloxy carbonyl-L-valine-L-alanine is an example.

The present invention also concerns the pharmaceutical composition and method of treatment of IL-1β protease mediated disease states or disorders in a mammal in need of such treatment comprising the administration of IL-1β protease inhibitors of formula (A) as the active agent. These disease states and disorders include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, immune-based diseases, such as hypersensitivity; auto-immune diseases, such as multiple sclerosis; bone diseases; and certain tumors and leukemias.

The present invention has particular utility in the modulation of processing of IL-1β for the treatment of rheumatoid arthritis. Levels of IL-1β are known to be elevated in the synovial fluid of patients with the disease. Additionally, IL-1β stimulates the synthesis of enzymes believed to be involved in inflammation, such as collagenase and PLA2, and produces joint destruction which is very similar to rheumatoid arthritis following intra-articular injection in animals.

In the practice of this invention an effective amount of a compound of the invention or a pharmaceutical composition thereof is administered to the subject in need of, or desiring, such treatment. These compounds or compositions may be administered by any of a variety of routes depending upon the specific end use, including orally, parenterally (including subcutaneous, intraarticular, intramuscular and intravenous administration), rectally, buccally (including sublingually), transdermally or intranasally. The most suitable route in any given case will depend upon the use, the particular active ingredient, and the subject involved. The compound or composition may also be administered by means of controlled-release, depot implant or injectable formulations as described more fully herein.

In general, for the uses as described in the instant invention, it is expedient to administer the active ingredient in amounts between about 0.1 and 100 mg/kg body weight, most preferably from about 0.1 to 30 mg/kg body weight for human therapy, the active ingredient will be administered preferably in the range of from about 0.1 to about 20–50 mg/kg/day. This administration may be accomplished by a single administration, by distribution over several applications or by slow release in order to achieve the most effective results. When administered as a single dose, administration will most preferably be in the range of from about 0.1 mg/kg to about 10 mg/kg.

The exact dose and regimen for administration of these compounds and compositions will necessarily be dependent upon the needs of the individual subject being treated, the type of treatment, and the degree of affliction or need. In general, parenteral administration requires lower dosage than other methods of administration which are more dependent upon absorption.

A further aspect of the present invention relates to pharmaceutical compositions comprising as an active ingredient a compound of the present invention in admixture with a pharmaceutically acceptable, non-toxic carrier. As mentioned above, such compositions may be prepared for use for parenteral (subcutaneous, intraarticular, intramuscular or intravenous) administration, particularly in the form of liquid solutions or suspensions; for oral or buccal administration, particularly in the form of tablets or capsules; or intranasally, particularly in the form of powders, nasal drops or aerosols.

When administered orally (or rectally) the compounds will usually be formulated into a unit dosage form such as a tablet, capsule, suppository or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, alginate, tragacanth, gelatin, syrup, methylcellulose, polyoxyethylene sorbitar monolaurate, methyl hydroxybenzoate, propyl hydroxybenzoate, talc, and magnesium stearate.

DETAILED DESCRIPTION OF THE INVENTION

As shown in Scheme 1, t-butyl hydrazine acetic acid (Formula 1, prepared according to Niedrich, H. et al., *Chem. Ber.* 102, 1557–1569 (1969)) was acylated with either an N-protected amino acid or dipeptide acid or any desired non-peptide carboxylic acid. The acylation reaction was carried out using a peptide coupling reagent such as an acid chloride, mixed anhydride and other methods described in *The Practice of Peptide Synthesis* (M. Bodanszky, Ed., 1984 Springer-Verlag, NY) to yield an acyl hydrazone (Formula 3). The acyl hydrazone in turn was reacted with an α-halo acetyl chloride (Formula 4) in the presence of a base such as N-methylmorpholine. This reaction afforded compounds of Formula 5. When compounds of Formula 5 were treated with trifluoroacetic acid (TFA) in methylene chloride (25% TFA solution) for 3 hrs. at 25° C., the t-butyl ester was hydrolyzed and the inhibitors of Formula 7 were obtained. Alternatively, when the acyl hydrazide of Formula 5 (W=Br) was treated with a phenol, arylcarboxylic acid, diarylphosphinic acid, a tetronic acid derivative or a 5-hydroxy-pyrazole derivative in dimethylformamide containing potassium fluoride, the compounds of the type described by Formula 6 were obtained. These t-butyl esters were then treated with TFA as before (Formula 5→7) to furnish inhibitors of Formula 7.

SCHEME 1

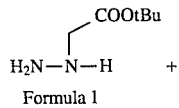
Formula 1

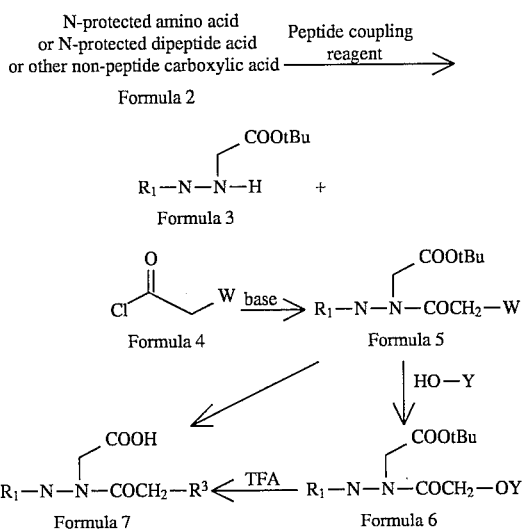

where
W=halo;
HO-Y=phenol, carboxylic acid, diarylphosphinic acid, tetronic acid derivative or 5-hydroxypyrazole derivative;
$R^1$ and $R^3$ are as defined previously.

The following examples further illustrate the compounds of the invention.

EXAMPLE 1

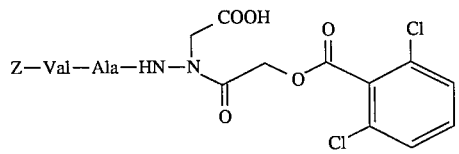

Z=N terminal protecting group N-benzyloxycarbonyl

N-Benzyloxycarbony-L-valine-L-alanine-azaaspartic acid 2,6-dichlorobenzoyloxymethyl ketone

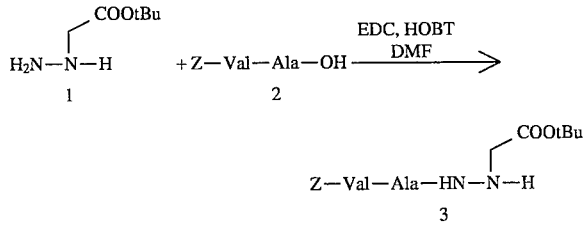

Part A

Z-Val-Ala-OH(2) (4.00 g, 12.4 mmol), hydrazine(1) (2.18 g, 14.9 mmol) and HOBT (2.09 g, 13.6 mmol) were dissolved in 25 mL of DMF. 1-(3-Dimethyl-aminopropyl)-3-ethyl carbodiimide hydrochloride (EDC, 2.61 g, 13.6 mmol) was then added in one portion at 0° C. and the reaction solution stirred for 6 h. The reaction solution was then poured into 800 mL of water and the product extracted into ethylacetate (3×). The organic layer was washed (water, 0.3 NaKHSO$_4$ (2×), 5% NaHCO$_3$ (2×), brine) and dried over Na$_2$SO$_4$. Evaporation of solvent yielded[3] as a fine white powder of sufficient purity: 5.34 g, 95%, MP 115°–157° C.

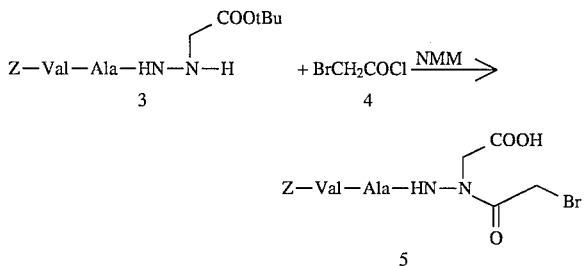

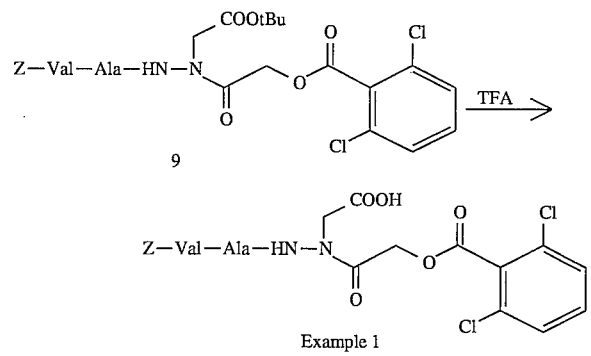

Part B

Bromoacetyl chloride(4) (0.71 mL, 8.66 mmol) was added dropwise to a 0° C. solution of hydrazide(3) (3.00 g, 6.66 mmol) and N-methylmorpholine (1.1 mL, 9.99 mmol) in dichloromethane (80 mL). After stirring for 5 h at 0° C., the reaction mixture was poured into water (600 mL) and the product extracted into ethylacetate (3×). The organic phase was then washed (water, 0.3 NaKHSO$_4$ (2×), 5% NaHCO$_3$ (2×), brine), dried with Na$_2$SO$_4$, filtered and concentrated. Recrystallization from warm ethylacetate/hexanes provided the bromoacetyl derivative(5) (3.11 g, 82%) as a white crystalline solid, MP 136°–138° C.

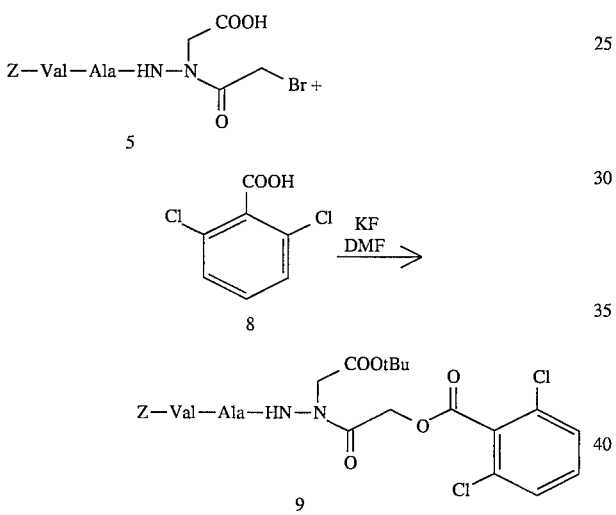

Part C

Powdered HF (0.128 g, 2.18 mmol) was added to a homogeneous solution of bromoacetyl derivative(5) (0.500 g, 0.874 mmol) and 2,6-dichlorobenzoic acid(8) (0.234-g, 1.20 mmol) in 5 mL of DMF. The reaction was then warmed at 60° C. for 10 hrs. The reaction mixture was poured into 100 mL of water and the products extracted into ethylacetate (3×). The ethylacetate layer was then washed (water, 0.3 NKHSO$_4$ (2×), 5% NaHCO$_3$ (2×), brine), dried with Na$_2$SO$_4$, filtered and concentrated. Recrystallization from warm EtOAc/hexanes provided dichlorobenzoate derivative(9) as a white crystalline solid (0.510 g, 86%, MP 176°–178° C.)

Part D

Toluene (5 mL) and a 25% solution of TFA/CH$_2$Cl$_2$ (100 mL) were added to a 250 mL flask containing tBu ester(9) (0.450 g, 0.66 mmol). After stirring for 1 hr at RT, additional toluene (50 mL) was added and all solvents evaporated under reduced pressure. Two additional 100 mL portions of toluene were added and evaporated. Concentration of a homogeneous solution of the product in dichloromethane and hexanes (2×) produced a fine white powder. After two-fold trituration with several mL of hexane, Example 1 was collected on a filter and dried under high vacuum: 0.411 g, 95% amorphous. Anal. calcd. for C$_{27}$H$_{30}$Cl$_2$N$_4$O$_9$: C, 51.85; H, 4.83; N, 8.46. Found C, 51.66; H, 5.14; N, 8.51.

Following the procedure described in Scheme 1 and by analogy to Example 1, the following compounds were prepared.

EXAMPLE 2

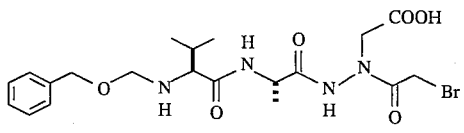

N-Benzyloxycarbonyl-L-valine-L-alanine-azaaspartic acid bromomethyl ketone

Anal. calcd. for C$_{20}$H$_{27}$BrN$_4$O$_7$.O$_2$H$_2$O: C, 46.29; H, 5.32; N, 10.80. Found: C,46.6, H, 5.50; N, 10.45.

EXAMPLE 3

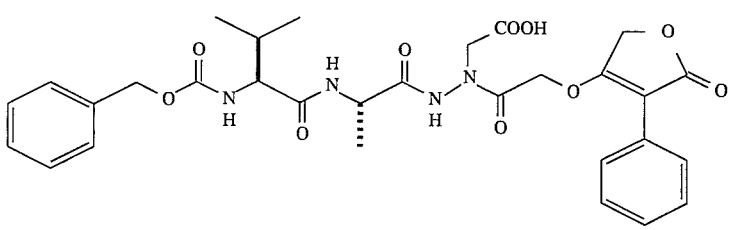

N-Benzyloxycarbonyl-L-valine-L-alanine-azaaspartic acid 4-(3-phenyl)tetronyloxymethyl ketone Anal. calcd. for C$_{30}$H$_{34}$N$_4$O$_{10}$·1H$_2$O: C, 57.32; H, 5.77; N, 8.91. Found: C, 57.28; H, 5.67; N, 9.02.

EXAMPLE 4

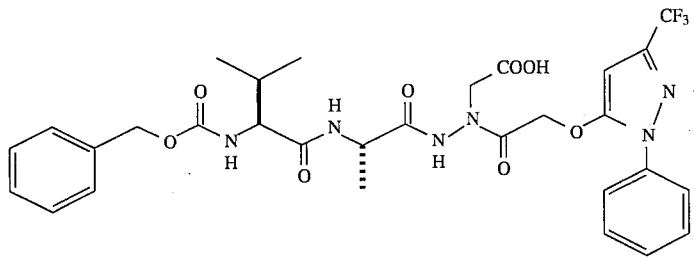

N-Benzyloxycarbonyl-L-valine-L-alanine-azaaspartic acid 5-(1-phenyl-3-trifluoromethyl)pyrazoloxymethyl ketone Anal. calcd. for $C_{30}H_{33}F_3N_6O_8 \cdot 0.5H_2O$: C, 53.65; H, 5.10; N, 12.51. Found: C, 53.94; H, 5.17; N, 12.24.

EXAMPLE 5

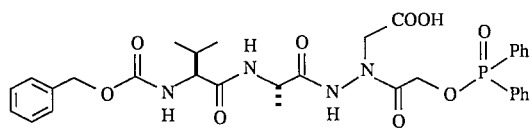

N-Benzyloxycarbonyl-L-valine-L-alanine-azaaspartic acid diphenylphosphinyloxymethyl ketone Anal. calcd. for $C_{32}H_{37}N_4O_9P \cdot 0.25\ H_2O$: C, 58.49; H, 5.75; N, 8.53. Found: C, 58.23; H, 5.87; N, 8.41.

EXAMPLE 6

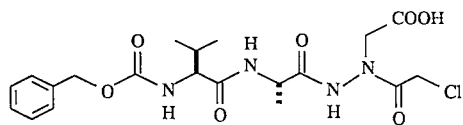

N-Benzyloxycarbonyl-L-valine-L-alanine-azaaspartic acid chloromethyl ketone mass spectrum m/z=471 (M+H)

EXAMPLE 7

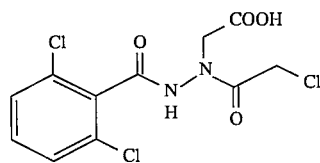

N-(2,6-Dichlorobenzoyl)-azaaspartic acid chloromethyl ketone mass spectrum m/z=338 (M+H)

In Vitro Testing

Second order rates for inactivation were obtained by using the enzyme assay described in Dolle, R. E. et al., *J. Med Chem.* 37,563 (1994).

The compounds in examples 1–7 possess IL-1β protease inhibition (kobs/I were>5,000$M^{-1}\ s^{1-1}$).

In Vitro

In vitro inhibition ($IC_{50}$) was determined as follows:

Human monocytes were isolated from heparinized leukopheresis units obtained through Biological Specialty Corporation (Lansdale, Pa). Monocytes were purified by Ficoll-Hupaque (Pharmacia Fine Chemicals, Piscataway, N.J.) gradient centrifugation and more than 95% pure monocyte populations obtained by centrifugal elutriation. The assay was performed on duplicate samples of freshly isolated human monocytes, cultured in suspension at 37° C. and rotated gently in conical bottom polypropylene tubes (Sardstedt Inc., Princeton, N.J.). Human monocytes at a concentration of 5×10⁶ cells/mL were resuspended in 1 mL of RPMI 1640 (a common tissue buffer from M.A. Bioproducts, Walkersville, Md.) containing 1% fetal calf serum (FCS) (HyClone, Logan, Utah) and 50 μg/mL gentamycin (Gibco, Grand Island, N.Y.). The cells were treated either with a compound of the invention (i.e. test compound) or with a non-inhibitor (control compound, typically 0.03% DMSO) for 15 minutes and then activated with 0.01% fixed *Staphylococcus aureus* (The Enzyme Center, Malden, Mass.) for 1 hour. The cells were then centrifuged and resuspended in 1 mL of cysteine, methionine-free RPMI media containing 1% dialyzed FCS (Hyclone). The cells were pretreated with a test compound or control compound for 15 minutes after which 0.01% fixed *S. aureus* plus 100 μCi Tran 35-S label (ICN, Irvine, Calif.) was added and the cells incubated at 37 ° C. for 1 hour. After incubation, cells were centrifuged, washed once in phosphate buffer saline and resuspended in 1 mL RPMI containing 1% fetal calf serum. The cells were again pretreated with a test or control compound for 15 minutes and then 0.01% *S. aureus* for 2 hours. At the end of the incubation, cells were centrifuged and supernates saved for immunoprecipitation. Cells were washed once in phosphate buffer saline and then lysed in RIPA, a continuous cell media buffer containing 2 mM phenyimethylsulfonyl fluoride, 10 mM iodoacetate, 1 μg/mL pepstatin A, 1 μg/mL leupeptin and 0.5 TIU aprotinin.

For the immunoprecipitations, an equal volume of 1% dry milk in RIPA buffer plus 50 μL of resuspended protein A sepharose CL-4B (Pharmacia, Piscataway, N.Y.) was added to supernates and 1 mL of 4% dry milk containing protein A sepharose CL-4B to cell lysates and samples rotated for 30 minutes at 4° C. Beads were then centrifuged down, samples transferred to fresh tubes and incubated overnight with 40 82 g rabbit anti-human IL-1β polyclonal antibody (Genzyme, Cambridge, Mass.). The IL-1β proteins were then precipitated with 70 μL protein A sepharose, resuspended in 60 μL SDS sample buffer and run on 15% SGD-PAGE gels. Autoradiography was performed on dried gels and the amount of radioactivity (counts per minute, cpm) quantitated using a Betascope 603 analyzer.

Data Analysis

In the monocyte pulse chase assay, each test parameter was run in duplicate. Data was collected from the Beta Scope using a personal computer, then transferred to the VAX system for calculation of mean cpm and standard deviation of the mean. When test compounds were evaluated, the percent inhibition of release of mature IL-1β was calculated as follows:

100 × [1 − (cells treated with stimuli + test compound − unstimulated cells)/ (cells treated with stimuli + control compound − unstimulated cells)]

These % inhibition values were then used to calculate $IC_{50}$ value for each compound. Since the human monocyte pulse chase assay uses primary cells from different donors, each test compound was run in 2–3 separate experiments, using monocytes from 2–3 different donors.

For examples given above, the in vitro $IC_{50}$'s ranged from approximately 0.1 up to approximately 10 μM.

We claim:

1. A compound of the formula (A) or a pharmaceutically acceptable salt thereof:

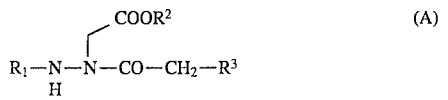

wherein:
$R_2$=H or alkyl;
$R^3$=halo, $O(CO)_{0-1}$ aryl, $OPOR^4R^5$,

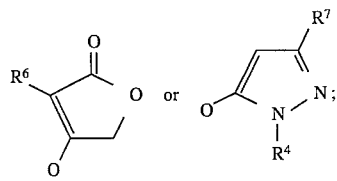

where
$R^4$ and $R^5$=aryl;
$R^6$=H, aryl or aralkyl;
$R^7$=$R^6$, $CF_3$ or $CF_2CF_3$;
$R^1$=$R^6$-CO, heteroaryl-CO, heteroaralkyl-CO or amino acid.

2. The compound of claim 1 wherein:
$R^2$=H;
$R^3$=O(CO) aryl; and
$R^1$=$R^6$-CO or amino acid where $R^6$ is aralkyl.

3. The compound of claim 1 wherein:
$R^2$=H;
$R^3$=halo; and
$R^1$=$R^6$-CO, heteroaryl-CO, or amino acid where $R^6$ is aralkyl.

4. The compound of claim 1 wherein:
$R^2$=H;
$R^3$=halo, $O(CO)_{0-1}$ aryl, $OPOR^4R^5$,

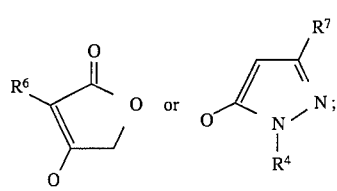

where
$R^6$=aryl;
$R^7$=$CF_3$; and
$R^1$=aralkyl-CO or amino acid.

5. The compound according to claim 1 selected from the group consisting of:
N-Benzyloxycarbonyl-L-valine-L-alanine-azaaspartic acid 2,6-dichlorobenzoyloxy-methyl ketone; N-Benzyloxycarbonyl-L-valine-L-alanine-azaaspartic acid bromomethyl ketone; N-Benzyloxycarbonyl-L-valine-L-alanine-azaaspartic acid 3-(2-phenyl)-tetronyloxymethyl ketone; N-Benzyloxycarbonyl-L-valine-L-alanine-azaaspartic acid 5-(1-phenyl-3-trifluoromethyl)pyrazoloxymethyl ketone; N-Benzyloxycarbonyl-L-valine-L-alanine-azaaspartic acid diphenylphosphinyloxymethyl ketone; N-Benzyloxycarbo-L-valine-L-alanine-azaaspartic acid chloromethyl ketone; and N-(2,6-Dichlorobenzoyl)-azaaspartic acid chloromethyl ketone.

6. A pharmaceutical composition for inhibiting interleukin-1β protease comprising a compound of the formula (A) defined in claim 1 in a pharmaceutically acceptable carrier.

7. A pharmaceutical composition for inhibiting interleukin-1β p protease comprising the compound defined in any of claims 2–5.

8. A method for inhibiting interleukin-1β protease activity in a mammal in need of treatment for inflammatory and immune-based diseases of lung, central nervous system, or connective tissue comprising administering to said mammal an effective interleukin-1β protease inhibitory amount of a composition comprising a compound of the formula (A) or a pharmaceutically acceptable salt thereof

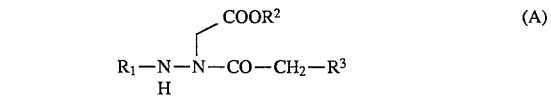

wherein:
$R_2$=H or alkyl;
$R^3$=halo, $O(CO)_{0-1}$ aryl, $OPOR^4R^5$,

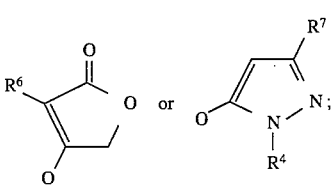

where
$R^4$ and $R^5$=aryl;
$R^6$=H, aryl or aralkyl;
$R^7$=$R^6$, $CF_3$ or $CF_2CF_3$;
$R_1$=$R^6$-CO, heteroaryl-CO, heteroaralkyl-CO or amino acid.

9. A method for inhibiting interleukin-1β protease activity in a mammal in need of treatment for inflammatory and immune-based diseases of lung, central nervous system, or connective tissue comprising administering to said mammal an effective interleukin-1β protease inhibitory amount of a composition comprising a compound defined in any of claims 2–5.

* * * * *